United States Patent [19]

Holtkamp, Sr.

[11] Patent Number: Plant 7,255

[45] Date of Patent: Jun. 26, 1990

[54] AFRICAN VIOLET PLANT NAMED SAMOA

[76] Inventor: Reinhold Holtkamp, Sr.,
Blumenstrasse 28, D 4242
Rees-Haffen, Fed. Rep. of Germany

[21] Appl. No.: 362,964

[22] Filed: Jun. 8, 1989

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Samoa characterized by its large, single violet-shaped, purple flowers with somewhat wavy edges and occasional fine white line on some petal edges; strong, upright flower stems that curve slightly toward the center to form a compact bouquet above the leaves; dark green, oval to heart-shaped leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Samoa.

The new cultivar was referred to during the breeding and selection process by the designation I 53/3 and is a product of a planned breeding program. The new cultivar was originated from a cross made by me in the controlled breeding program in Haffen, Federal Republic of Germany. The female, or seed parent was a cultivar designated H 79/3. The male, or pollen parent was a cultivar designated XXI/3.

Samoa was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Samoa has not been observed under all possible environmental conditions. The phenotype may vary significantly with variations in environment such as temperature, light intensity and day length. The following observations, measurements and values described the new cultivar as grown in Haffen, West Germany and Nashville, Tenn. under greenhouse conditions which closely approximate those generally used in commercial practice.

The following traits have been repeatedly observed and are determined to be basic characteristics of Samoa, which in combination distinguish this African violet as a new and distinct cultivar:

(1) Strong, upright flower stems curving slightly toward the center.

(2) Large, single violet-shaped, purple flowers with somewhat wavy edges and occasional fine white line on some petal edges.

(3) Profuse flowering.

(4) Each plant carries 7–8 and more upright flower stems each of which carries 7–9 and more flowers.

(5) Long lasting; non-dropping flowers.

(6) Vigorous and compact grower.

(7) Plant saleable 10 to 11 weeks after potting.

(8) Seed capsules push slightly through.

(9) Dark green, oval to heart-shaped leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Color Chart (RHS), except where general colors of ordinary significance are referred to. Color values were taken under natural sunlight conditions at approximately 1 p.m. in Nashville, Tenn.

Botanical classification: *Saintpaulia ionantha,* Ramat., c.v. Samoa.

Parentage:

*Male parent.*—XXI/3.

*Female parent.*—H 79/3.

Propagation: The new cultivar holds its distinguishing characteristics through successive propagations by leaf cuttings.

Plant: From 10 cm to 12 cm tall when grown in pots, and approximately 25–30 cm in diameter when fully grown.

*Leaves.*—General form: Ovel to heart-shaped. Diameter: 60–70 mm wide and 70–80 mm long. Texture: Leatherlike. Aspect: Shiny, hairy, slightly serrated. Veins: Upperside: visible; underside: well pronounced, light green, shiny. Color (upperside): Yellow-Green Group 147 A. Color (underside): Greyed-Green Group 186 A. Petiole: Strong upright, green with purplish brown touch, hairy.

*Flowers.*—Buds: Bell-shaped, 5–7 mm just before opening. Sepals: Five (5). Color: Purplish brown. Calyx: Shape: Funnel-shaped Aspect: Spear-shaped, hairy. Peduncle: Character: Strong upright, hairy. Color: Purplish brown. Individual flowers: Size: Approximately 45 mm. Shape: Single violet-shaped with somewhat wavy edges. Color (upperside): Between Purple-Violet Group 80 A and 81 A. The center is almost as dark as Purple Group 79 A. Under cooler temperatures and more intensive lighting, the purple tends to intensify. Color (underside):

Borne: Each flower stem carries 7–9 and more flowers on strong, upright peduncle that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsules push slightly through. Filaments: Yellowish green, 3–4 mm long. Pollen color: Yellow Group 7 A. Styles: 7–8 mm long, dark purple, base of ovary light green and hairy.

*Roots.*—Normally developed, white when young, turning slightly brownish when older.

Disease resistance: Good.

General observations: Samoa has an extremely attractive appearance due to its large, single violet-shaped, purple flowers contrasting nicely with the bright yellow anthers. The center is darker purple with an occasional additional very small petal. The petal edges are somewhat wavy and sometimes have a fine white line. A tight bouquet of flowers free standing above the leaves develops after approximately 10–11 weeks. Each of the 7–8 and more strong flower stems carries 7–9 and more flowers which are long-lasting and non-dropping. The bouquet is surrounded by dark green, oval to heart-shaped leaves. The seed capsules push slightly through.

I claim:

1. A new and distinct cultivar of African violet named Samoa, as described and illustrated, and particularly characterized by its large, single violet-shaped, purple flowers with somewhat wavy edges and occasional fine white line on some petal edges; strong, upright flower stems that curve slightly toward the center to form a compact bouquet above the leaves; dark green, oval to heart-shaped leaves; profuse flowering, vigorous and compact growth habit, flowering 10–11 weeks after potting, and its long lasting and non-dropping flowers.

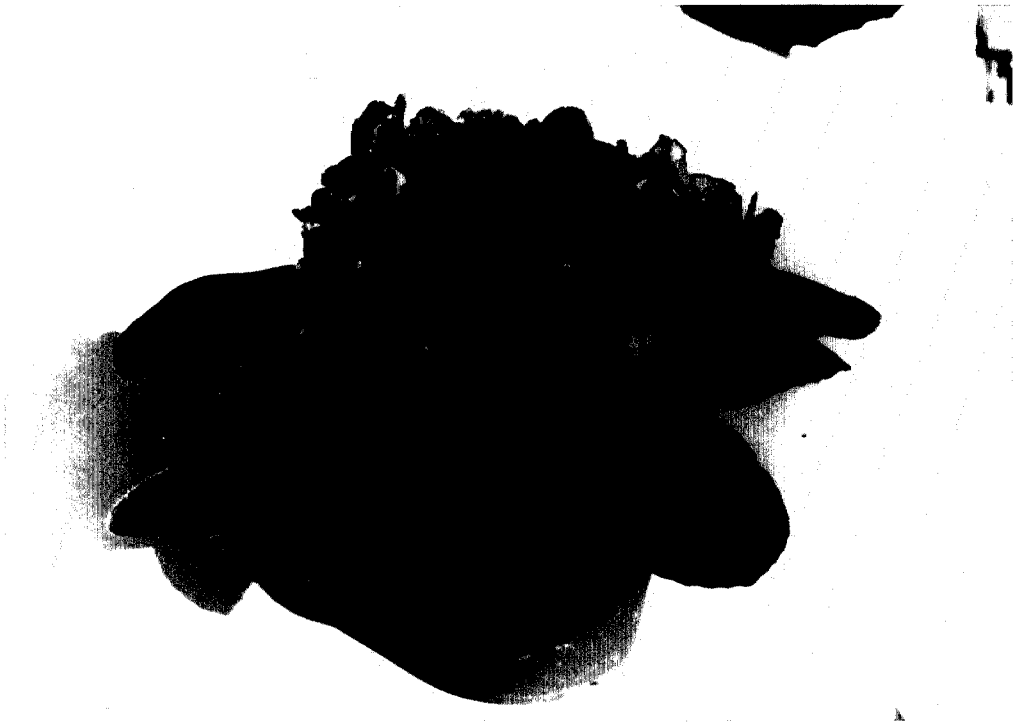

* * * * *